(12) United States Patent
Soukup

(10) Patent No.: US 8,203,005 B2
(45) Date of Patent: Jun. 19, 2012

(54) MANUFACTURING PROCESS FOR ENANTIOMERICALLY PURE 8-ARYLOCTANOIC ACIDS AS ALISKIREN

(75) Inventor: Milan Soukup, Sarasota, FL (US)

(73) Assignee: Carbo Design LLC, Sarasota, FL (US)

( * ) Notice: Subject to any disclaimer, the term of this patent is extended or adjusted under 35 U.S.C. 154(b) by 0 days.

(21) Appl. No.: 12/925,153

(22) Filed: Oct. 15, 2010

(65) Prior Publication Data
US 2011/0105767 A1 May 5, 2011

Related U.S. Application Data

(60) Provisional application No. 61/279,995, filed on Oct. 29, 2009.

(51) Int. Cl.
C07C 231/02 (2006.01)
C07D 405/04 (2006.01)
C07D 307/33 (2006.01)
(52) U.S. Cl. .................... 548/517; 549/321; 564/157
(58) Field of Classification Search .................... None
See application file for complete search history.

(56) References Cited

U.S. PATENT DOCUMENTS 5,559,111 A 9/1996 Göschke et al.

FOREIGN PATENT DOCUMENTS

| CA | 2 634 513 A11 | 12/2009 |
|---|---|---|
| EP | 0 678 503 B1 | 9/1999 |
| EP | 0678503 B1 | 9/1999 |
| EP | 1215201 B1 | 10/2006 |
| EP | 1 958 666 A1 | 8/2008 |
| EP | 1958 666 A1 | 8/2008 |
| EP | 2 062 874 | 5/2009 |
| GB | 2 431 640 A | 5/2007 |
| GB | 2 431 641 A | 5/2007 |
| GB | 2 431 642 A | 5/2007 |
| GB | 2 431 643 A | 5/2007 |
| GB | 2 431 644 A | 5/2007 |
| GB | 2 431 645 A | 5/2007 |
| GB | 2 431 646 A | 5/2007 |
| GB | 2 431 647 A | 5/2007 |
| GB | 2 431 648 A | 5/2007 |
| GB | 2 431 649 A | 5/2007 |
| GB | 2 431 650 A | 5/2007 |
| GB | 2 431 651 A | 5/2007 |
| GB | 2 431 652 A | 5/2007 |
| GB | 2 431 653 A | 5/2007 |
| GB | 2 431 654 A | 5/2007 |
| WO | WO01/09079 A1 | 2/2001 |
| WO | WO01/09083 A1 | 2/2001 |
| WO | WO02/02487 A1 | 1/2002 |
| WO | WO02/02500 A1 | 1/2002 |
| WO | WO 02/02500 A1 | 1/2002 |
| WO | WO02/02508 A1 | 1/2002 |
| WO | WO02/08172 A1 | 1/2002 |
| WO | WO 02/092828 A2 | 11/2002 |
| WO | WO 03/103653 A1 | 12/2003 |
| WO | WO 2005/090305 A1 | 9/2005 |
| WO | WO2006/024501 A1 | 3/2006 |
| WO | WO2006/095020 A1 | 9/2006 |
| WO | WO 2006/131304 A2 | 12/2006 |
| WO | WO 2007/006532 A1 | 1/2007 |
| WO | WO2007/039183 A1 | 4/2007 |
| WO | WO2007/045420 A2 | 4/2007 |
| WO | WO2007045420 | * 4/2007 |
| WO | WO2007/048620 A1 | 5/2007 |
| WO | WO2007/054254 A1 | 5/2007 |
| WO | WO2007/118681 A1 | 10/2007 |
| WO | WO2008/119804 A1 | 10/2008 |
| WO | WO2008/155338 A2 | 12/2008 |
| WO | WO2009/049837 A2 | 4/2009 |

OTHER PUBLICATIONS

H. Ruger et al. Tetrahedron Letters, 2000, 41, 100085.
D.A. Sandham et al. Tetrahedron Letters, 2000, 41, 10091.
A. Dondoni et al. Terahedron Letters, 2001, 42, 4819.
Drugs future, 2001, 26(12).
S. Henessian et al. J. Org. Chem. 2002, 67, 4261.
R. Goschke et al. Helv. Chim. Acta 2003, 86, 2848.
Hua Dong et al. Tetrahedron Letters 2005, 46, 6337.
K.B. Lindday et al. J. Org. Chem. 2006, 71, 4766.
J.A. Boogers et al. Org. Process &Develop. 2007, 11, 585.
A. Andrusko et a. Tetrahedron letters 2008, 49, 5980.
TCI Reagent Gude 2009-2010, 50-66 16-17 85-89 90-93.
J. Advanced Org. Chem. J Wiley&sons NY 1991, p. 1209-1211.
Hoben-Weyl, Methoden der Org. Chemie, 4th Ed., Synthese von Peptiden1, vol. 15/II (1974), vol. IX (1955), vol. E11 (1985), Thieme Verlag.
E.Gross The Peptides, vol. 1 and 2, Academic Press .London 1970/80.
M.Bohdansky,Princelpes of Peptide Synthesis, SpringerVerlag, Berlin 1984.
N.J. Manesis et al. J. Org. Chem. 1987, 52, 5331.
M. Kim et al. Archiv of Pharm. Res. 2004, 27, 151.
D.J. Ager etal. Org. Process Res. & Develop. 2004, 8, 72.
J. Kaiser et al. Microbiol. Rev. 1966, 60(3), 483.
D. Billeret et al. J. Heterocycl. Chem. 1993, 30, 671.
Mcomie, Protective Groups in Org. Synthesis, 1999.
W. Greene et al. Protective Groups in org. Synthesis, 3rd Ed. J. Wiley&Sons 1999, p. 17-245, 494-653.
Ch.T. West et al., J. Org. Chem. 1973, 38, 2675.
J. Fry et al. J Org. Chem. 1978, 43, 374.
G. Olah, et al. Synthesis, 1986, 770.
A. On et al. Synthesis, 1987, 736.
H. Firouzabadi et al. Tetrahedron 2004, 60, 10843.
H. Fillon et al. Tetrahedron 2003, 59, 8199.

(Continued)

Primary Examiner — Sun Jae Loewe

(57) ABSTRACT

The invention describes a novel technical process and novel intermediates useful for the manufacture of enantiomerically pure 8-aryloctanoic acids of the formula I which are pharmaceutically active compounds as rennin inhibitors.

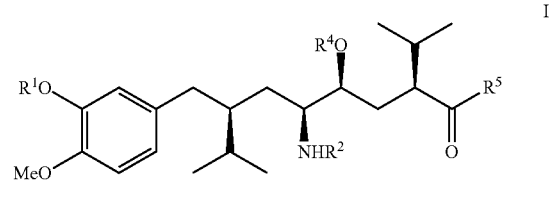

5 Claims, No Drawings

OTHER PUBLICATIONS

G.A. Kraus et al. Tetrahedron letters 2002, 43, 7077.
S. Repichet et al. Tetrahedron Letters, 2003, 44, 2037.
K. Kageyama et al. J. Org Chem. 1975, 40, 1932.
J. Vekemans et al. J. Org. Chem. 1990, 55, 5336.
J. Sauter et al., JACS 1959, 81, 3677.
J. Sauter et al. JACS 1959, 81, 3881.
M. Shah et al. Tetrahedron Letters 1986, 27, 5437.
E,J; Corey et al. Tetrahedron letters 1980, 21, 1819.
P.A. Evans et al. Tetrahedron Letters 1999, 40, 1253.
P.A. Evans et al. Tetrahedron Letters 1997, 38, 5249.
M. Maier et al. Synlett 1995, 1029.
H. Sheldrake et al. Org. Biomol. Chem. 2009, 7, 205.
S. Behr et al. Eur. J. Org Chem. 2004, 3884.
M.T. Barros et al. Tetrahedron 2009, 65, 396.
J.M. Holland et al. J. Org. Chem. 2003, 68, 747.
T.J. Donohoe et al. Org. Lett. 2009, 11, 2305.
S. Nahm et al. Tetrahedron Letters 1981, 22, 3815.
J.A. Murphy et al. Org. Letters 2005, 7, 1427.
R. Chenevert et al. J. Org. Chem. 1996, 61, 1219.
E. Vedejs et al. J. Am. Chem. Soc. 1996, 1809.

* cited by examiner

MANUFACTURING PROCESS FOR ENANTIOMERICALLY PURE 8-ARYLOCTANOIC ACIDS AS ALISKIREN

This application claims priority to U.S. Provisional Application Ser. No. 61/279,995 filed Oct. 29, 2009.

BACKGROUND OF THE INVENTION

8-Aryloctanoic acids of a general formula I, having the 2S,4S,5S,7S-configuration

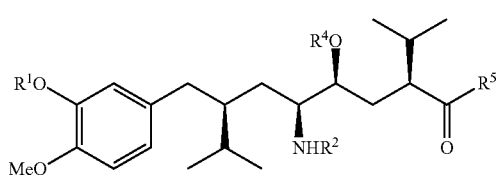

I especially compound such as Aliskiren, wherein $R^1$ represents $CH_3OCH_2CH_2CH_2$—, $R^2$ and $R^4$ hydrogen and $R^5$—$NHCH_2C(CH_3)_2CONH_2$, (INN name: 5-amino-N-(2-carbamoyl-2-methylpropyl)-4-hydroxy-2-isopropyl-7-[4-methoxy-3-(3-methoxypropoxy)benzyl]-8-methyl-nanoamide), are excellent new antihypertensive which interfere with the rennin-angiotensin system.

After discovery of the biological activity of compounds of general formula I in 1994, first synthesis of Aliskiren has been also disclosed (U.S. Pat. No. 5,559,111 and EP 0 678 503). Since Aliskiren contains 4 chiral centers, synthesis of enantiomerically pure compound is very complex: After 2001 many patents and publications have been filed or published claiming alternative routes to Aliskiren (WO 01/09083, WO 01/09079, EP 1 215 201, WO 02/02508, WO 02/02500, WO 02/02487, WO 02/08172, WO 02/092828, WO 02/02500, WO 03/103653, UK 2 431 640, GB 2 431 641, GB 2 431 642, GB 2 431 643, GB 2 431 644, GB 2 431 645, GB 2 431 646, GB 2 431 647, GB 2 431 48, GB 2 431 649, GB 2 431 650, GB 2 431 651, GB 2 431 652, GB 2 431 653, GB 2 431 654, WO 2005/054177, WO 2005/090305, WO 2005/ 051895, WO 2006/131304, WO2006/095020, WO2006/024501, WO2007/054254, WO2007/039183, EP 2 062 874, EP 1958 666, WO 2007/006532, WO2007/045420, WO2008/155338, WO2008/119804, CA 2 634 513, WO2007/048620, WO2007/118681, EP2189442, US2009/0076062, WO2009/ 049837, WO2010/010165, Tetrahedron Letters 2000, 41, 10085, ibid. 2000, 41, 10091, ibid. 2001, 42, 4819, Drugs Fut. 2001, 1139, J. Org. Chem. 2002, 67, 4261, Helv. Chim Acta 2003, 86, 2848, Tetrahedron Letters 2005, 46, 6337, J. Org. Chem. 2006, 71, 4766, Organic Process & Develop 2007, 11, 584, Tetrahedron Letters 2008, 49, 5980 and Org. Lett. 2010, 12, 1816). Nevertheless, none of them fulfill requirements for a short and cost effective manufacturing process.

SUMMARY OF THE INVENTION

The present invention discloses a novel very efficient process for the manufacture of enantiomerically pure compounds of general formula I, specifically of Aliskiren, as shown in Scheme 1:

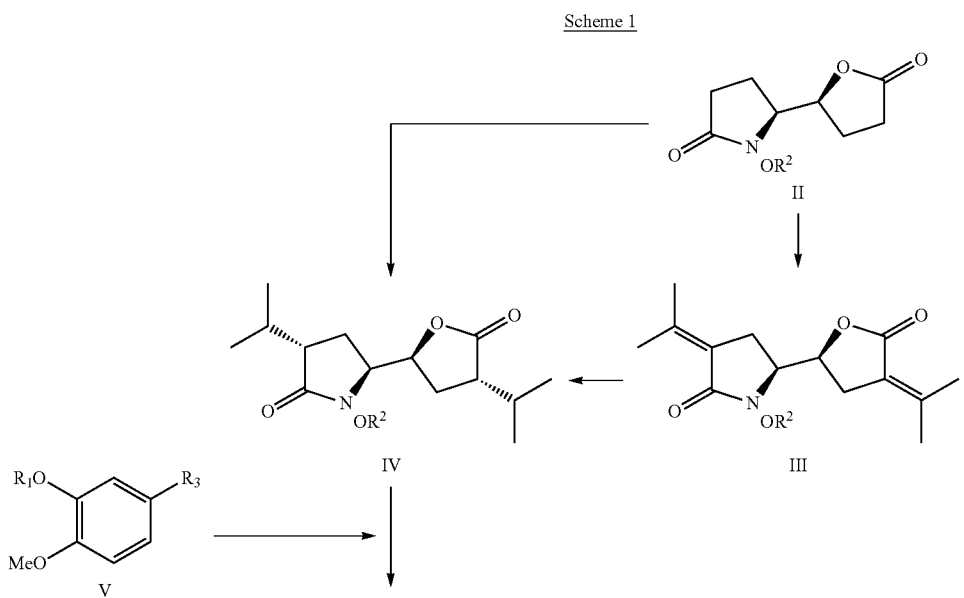

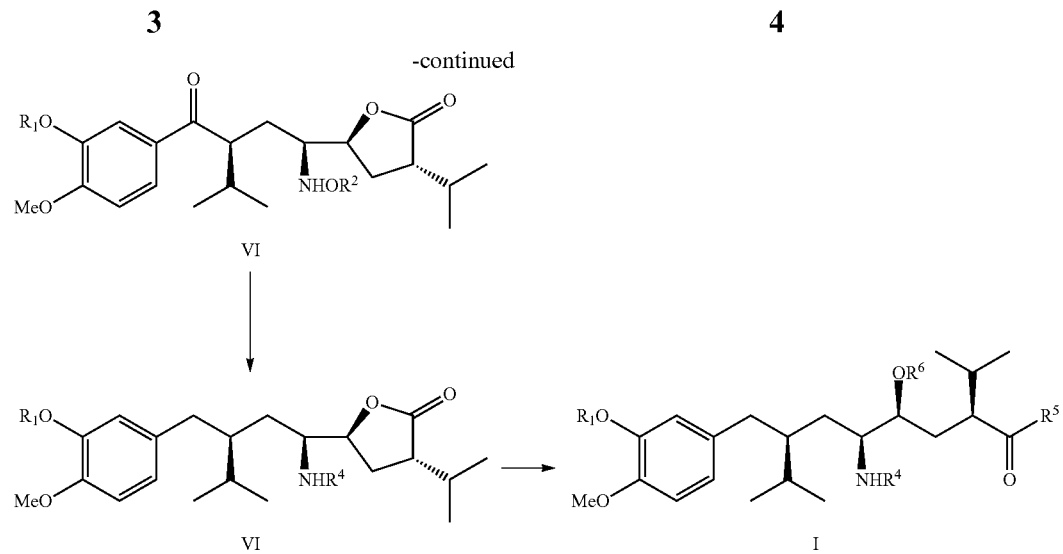

It has been unexpectedly found that the compounds of formula I, and intermediates thereof (formulas IV, VI and VII), can be prepared in a very efficient way from a new bicyclic compound of general formula II, a precursor containing only two chiral centers: In alkylation step these two centers control diastereoselective formation of a third and fourth chiral centers providing enantiomerically pure key compound of formula IV which can be easily converted into the final compound of formula I.

The compound of formula II is accessible from inexpensive starting materials as shown in Scheme 2: Thus, either prochiral bislactone of formula VIII can be desymmetrized, via compound of formula IX, or compound of formula XIII can be rearranged into enantiomerically pure compound of formula II (or also X).

Scheme 2

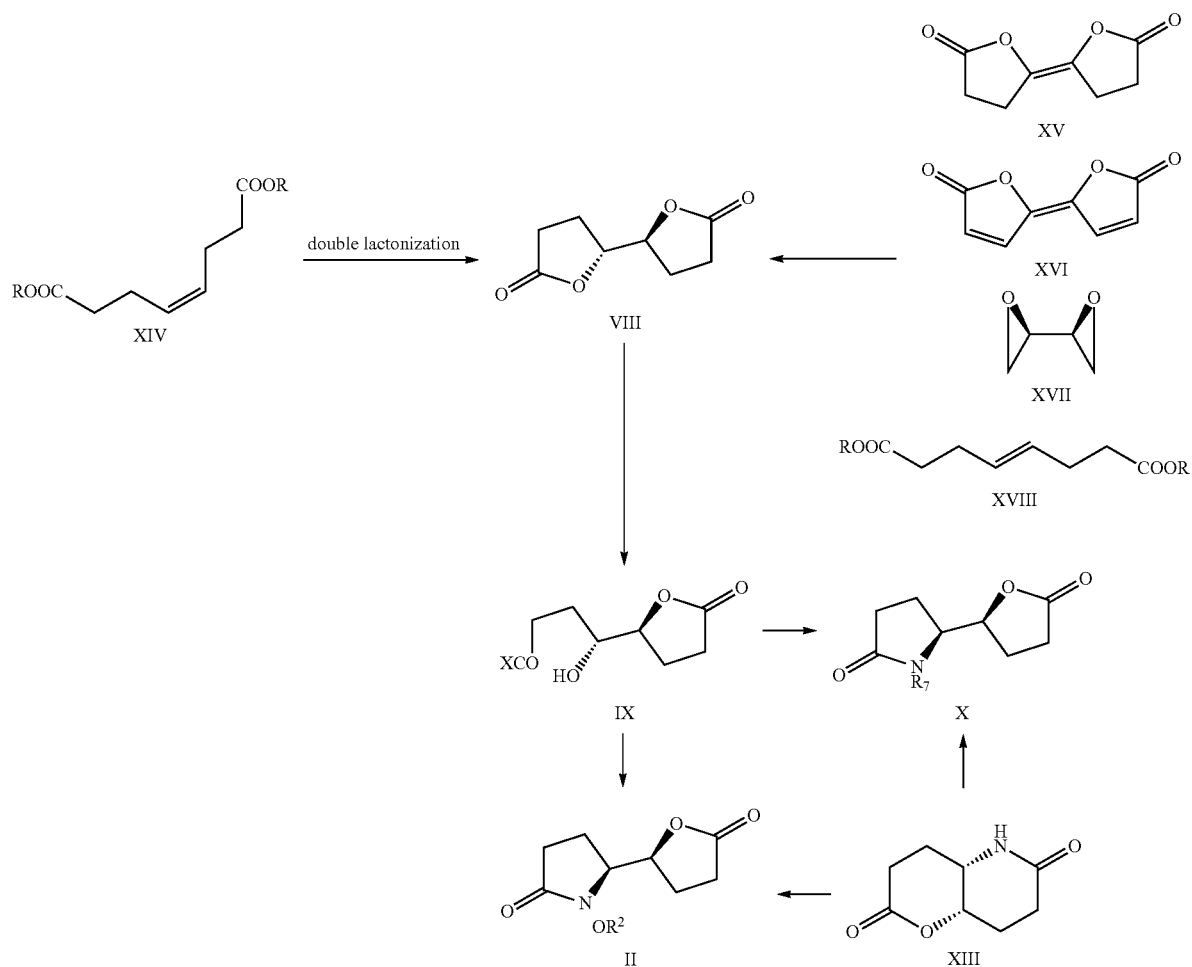

The invented process as shown in Schemes 1 and 2 can also be applied for preparation of racemic compounds of formulas II, III, IV, VI and VII which can be alternatively subjected at any stage of the synthesis to a resolution step.

DETAILED DESCRIPTION OF THE INVENTION

The present invention claims a new process for the preparation of a compound of general formula I

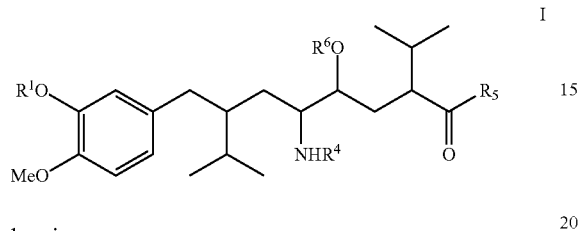

wherein $R^1$ represents hydrogen, linear or brunched $C_{1-6}$ alkyl, $C_{1-6}$ alkoxy-$C_{1-6}$-alkyl, aryl, alkylaryl, arylalkyl, preferably $CH_3OCH_2CH_2CH_2—$, acyl, carbamoyl, trifluoracetyl, mesyl, tosyl, trifluoromethanesulfonyl, trialkylsilyl or alkylarylsilyl;

$R^4$ represents hydrogen, alkyl, aryl, alkylaryl, arylalkyl, trialkylsilyl, alkylarylsilyl, hydroxy, alkoxy, aryloxy, arylalkoxy, alkylaryloxy, trialkylsilyloxy, with heteroatom(s) substituted alkyl, alkylaryl, arylalkyl, preferably benzyl, mono-, di- or tri-methoxybenzyl, or another N-protective group, in particular one which together with N forms an amide or carbamate as —C(O)H, —C(O)-alkyl, —C(O)-aryl, —C(O)-alkylaryl, —C(O)-arylalkyl, —C(O)—Oalkyl, —C(O)—Oaryl, —(O)C—Oalkylaryl, —C(O)—Oarylalkyl, preferably formyl, —C(O)Obenzyl (Cbz) or —C(O)O-tert.butyl (BOC), or —OC(O)-alkyl, —OC(O)-aryl, —OC(O)-alkylaryl, —OC(O)-arylalkyl, —OC(O)—Oalkyl, —OC(O)—Oaryl, —OC(O)—Oalkylaryl, —OC(O)—Oarylalkyl;

$R^5$ represents hydroxy, linear or brunched $C_{1-6}$ alkyloxy, aryloxy, alkylaryloxy, arylalkyloxy or trialkylsilyloxy or halogen, —$NH_2$, —$NMe_2$, preferably —$NHCH_2C(CH_3)_2CONH_2$;

$R^6$ represents hydrogen, arylalkyl, preferably benzyl, mono-, di-substituted benzyl, or another O-protective group, in particular one which together with O forms an ester or carbonate as —C(O)-alkyl, —C(O)-aryl, —C(O)-alkylaryl, —C(O)-arylalkyl, —C(O)—Oalkyl, —C(O)—Oaryl, —(O)C—Oalkylaryl, —C(O)—Oarylalkyl, preferably formy, acetyl, —C(O)Obenzyl (Cbz) or —C(O)O-tert.butyl (BOC), trifluoracetyl;

comprising following steps:
a) reaction of a compound of formula II

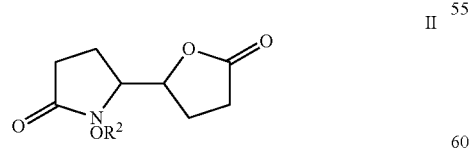

wherein $R^2$ represents hydrogen, alkyl, aryl, alkylaryl, trialkylsilyl, alkylarylsilyl, with heteroatom(s) substituted alkyl, aryl, alkylaryl, arylalkyl, preferably methyl, benzyl, mono-, di- or tri-methoxybenzyl or other O-protective group, in particular one which together with O forms an ester or carbonate, as —C(O)-alkyl, —C(O)-aryl, —C(O)-alkylaryl, —C(O)-arylalkyl, —C(O)—Oalkyl, —C(O)—Oaryl, —C(O)—Oalkylaryl, —C(O)—Oarylalkyl, preferably formyl, acetyl, —C(O)Obenzyl (Cbz) or —C(O)O-tert.butyl (BOC); either 1) with acetone under basic conditions followed by dehydration step providing a compound of formula III, wherein $R^2$ is the same as defined for compound of formula II

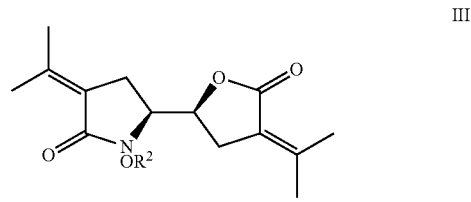

in which then the double bond is then hydrogenated or reduced to a single bond or
2) alternatively with a strong organic or inorganic base, preferably organic lithium or sodium amides as e.g. LDA or LiHMDS or NaHMDS, followed by alkylation with isopropyl halide, preferably bromide or iodide, providing compound of formula IV, wherein $R^2$ is the same as defined for compound of formula II

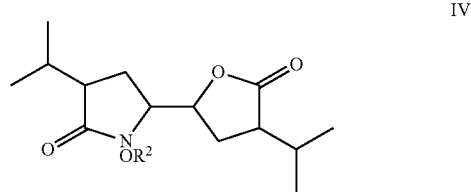

b) reaction of the compound of formula IV with compound of formula V,

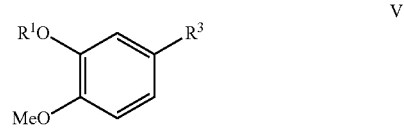

wherein $R^1$ is the same as defined for the compound of formula I and $R^3$ is a metal containing group such as —Li, —Na, —Mghalide, magnesatehalide, —Znhalide, —Cehalide, boronic acid as e.g. —B(OH)2, cuprate —Cuhalide, providing a compound of formula VI

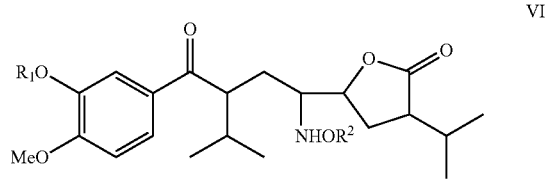

wherein, $R^1$ is the same as defined in compound of formula I and $R^2$ is the same as defined for compound of formula II, c) reduction or/and hydrogenation of C(8)-oxo and C(5)-hydroxylamine group in the compound of formula VI to a compound of formula VII,

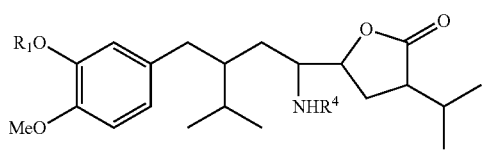

VII wherein $R^4$ represents hydrogen, alkylaryl, trialkylsilyl, alkylarylsilyl, with heteroatom(s) substituted alkylaryl, arylalkyl, preferably benzyl, mono-, di- or tri-methoxybenzyl, or other N-protective group, in particular one which together with N forms an amide or carbamate, as —C(O)-alkyl, —C(O)-aryl, —C(O)-alkylaryl, —C(O)-arylalkyl, —C(O)—Oalkyl, —C(O)—Oaryl, —C(O)—Oalkylaryl, —C(O)—Oarylalkyl, preferably formal, acetyl, —C(O)Obenzyl (Cbz) or —C(O)O-tert.butyl (BOC), or —$OR^2$, wherein $R^2$ is the same as defined for compound of formula II;

d) protection of C(5)-amino group followed by either
1) opening of the lactone of formula VII and reaction of free carboxylic acid with a peptide coupling reagent and $R^5$—H, wherein $R^5$ is the same as defined for compound of formula I, preferably with $NH_2CH_2C(CH_3)_2CONH_2$ or
2) by direct reaction of the lactone of formula VII with $R^5$—H, preferably with $NH_2CH_2C(CH_3)_2CONH_2$ When referring to compounds described in the present invention, it is understood that references are also being made to salts thereof.

Depending on the choice of starting materials the compounds can be present in the form of one possible isomers or a mixture thereof, for example as enantiomerically pure compound or as isomer mixtures, such a racemates, diastereomer mixtures etc., depending on the number of asymmetric carbon atoms.

In this invention racemic compounds of formulas II, III, IV, VI and VII can be subjected at any stage of the synthesis to a resolution or separation step using (chiral) agent or an enzymatic step or another separation method known as e.g. preparative HPLC or SMB etc. As the resolution agent any chiral acid or base, as commonly used for resolution of nitrogen- or alcohol- or carboxylate-containing compounds (e.g. TCI Reagent Guide 2009-2010, p. 50-56), can be used.

In this invention a characteristic of protective groups is that they can be removed readily (without the occurrence of undesired secondary reactions) for example by solvolysis, reduction, or alternatively under physiological conditions (as e.g. enzymatic cleavage or formation). Different protective groups can be selected so that they can be removed selectively at different stages of the synthesis while other protective groups remain intact. The corresponding alternatives can be selected readily by a person skilled in the art from those given in the standard reference works mentioned in literature (as e.g. Mc Omie "Protective Groups in Organic Chemistry" or Green et al. "Protective Groups in Organic Synthesis") or in the description or in the claims or the Examples.

In a preferred further embodiment of the invention, preparation of enantiomerically pure compound of general formula I,

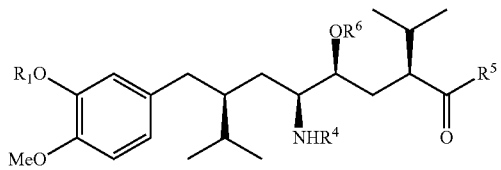

wherein $R^1$, $R^4$, $R^5$ and W are the same as defined for the compound of general formula I and the compounds of formulas II, III, IV, VI and VII have the configuration as defined in Scheme 1, can be carried out:

The enantiomerically pure bicyclic compound of formula II,

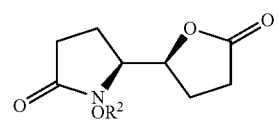

II having two chiral centers, can be deprotonated with a strong organic or inorganic base, preferably LDA or LiHMDS or NaHMDS, in a aprotic organic solvent, preferably THF at temperature between −50-0° C. and then stereoselectivly alkylated in situ with isopropyl halide, preferably isopropyl iodide, leading to compound of formula IV. The alkylation with isopropyl halide proceeds with high stereo selectivity control at third and fourth chiral centers resulting in one single stereo isomer IV with following configuration:

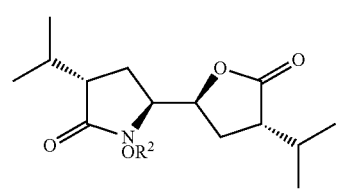

IV

Alternatively, the chiral compound of formula IV can also be prepared stereoselectivly in a process comprising deprotonation of the chiral compound of formula II with organic or inorganic base followed by condensation with acetone, dehydration and final hydrogenation (or chemical reduction) of the double bond.

In the next step the enantiomerically pure compound of formula IV can be reacted with compound of formula V, in analogy as reported in U.S. Pat. No. 5,559,111 (p. 78) or WO2007/045420 (p. 64, 67-8) providing the chiral compound of formula VI

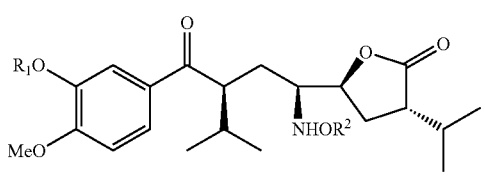

VI which is then subjected reduction and/or hydrogenation leading to enantiomerically pure compound of formula VII

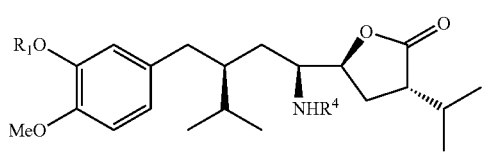

The compound of formula V, wherein $R^3$ is metallic radical, especially an alkali or earth alkali as e.g. lithium, sodium, potassium or a group of the formulas Mg-halogen, preferably bromine, is prepared from the corresponding aromatic halide (a compound of formula V, wherein $R^3$ is a halide, preferably bromide) and is used in situ in an ethereal solvent, such as THF or toluene, at a temperature range of −78° C. to 0° C. similar as reported in Novartis patent (p. 30, 78 and 82 U.S. Pat. No. 5,559,111). To reach good selectivity in Grignard reaction, Lewis acid catalysts, which are compatible with organometallic reagent, as e.g. bortrifluoro etherate or preferably Ce-halides as e.g. $CeCl_3$ can be added, prior to the reaction of compound of formula V with compound of formula IV.

The reduction of C(8)-oxo group and alternatively also C(5)-$NHOR^2$ group into C(5)-$NHR^4$ group in the compound of formula VI can be achieved simultaneously or in a few separate reductive steps analogues as reported in WO2007/045420 (p. 30-35): Typically, hydrogenation or/and reduction with a hydride can be employed whenever the term "reduction" is used in general terms in this application. It might include both a hydrogenation and/or reduction with hydride (e.g. Synthesis 1987, 736 and J. March, j. Wiley&Sons, NY 1992, Advanced Org. Chemistry j. Wiley&sons, NY 1991, p. 1209-1211).

A preferred reduction methods for the C(8)-oxo and/or C(5)-N—O groups are hydrogenation in the presence of homogeneous or heterogeneous hydrogenation catalysts. Catalyst for hydrogenation can be $PtO_2$ or 10% Pd—C or even Ra—Ni in polar or apolar solvents, preferably glacial acetic acid or alcohols, at rt or slightly elevated temperature under normal pressure or until 10 bar pressure.

Also chemical reduction with alkali or earth alkali metal hydrides, preferably sodium or lithium borohydride, DIBAH, triethylaluminium can be carried out. This reduction can also be accomplished with trialkylsilane, preferably triethylsilane, in protic or aprotic solvents, preferably chlorinated hydrocarbons as dichloromethane, in the presence of acids, preferably trifluoromethane sulphonic acid, trifluoro acetic acid or even Lewis acids as e.g. bortrifluoro etherate, $ZnCl_2$, $ALCl_3$, $TiCl_4$, $Yb(OTf)_3$ (TCI Reagent Guide 2009, p. 16-17, J. Org. Chem. 1973, 38, 2675, ibid. 1978, 43, 374, Synthesis 1986, 770), at reaction temperature between −78 C until reflux, preferably rt.

The compound of formula VII, after prior protection of the C(5)-amino group, can be converted into the compound of formula I comprising opening of the 5-membered lactone ring and reaction of the free carboxylic acid (or alternatively an ester thereof) with $R^5$—H as commonly known for preparation of amides using known coupling reagents (e.g. as already described in U.S. Pat. No. 5,559,111 and TCI Reagent Guide 2009, p. 85-89). The C(5)-amino protected free carboxylic acid can be reacted with $R^5$—H, preferably 3-amino-2,2-dimethylpropionamide, according to standard peptide coupling method as also described for this step in U.S. Pat. No. 5,559,111 on page 22 - 25 or, as reported in Houben-Weyl, Methoden der organischen Chemie, $4^{th}$ Edition, Synthese von Peptiden1, Volume 15/II (1974), Volume IX (1955), Volume E 11 (1985), Gerge Thieme Verlag, Stuttgart, The Peptides, (e. Gross and J. Meienhofer) Volume 1 and 2, Academic Press, London 1979/1980 or M. Bodansky Principels of Peptide Synthesis, Springer Verlag, Berlin 1984. The condensation of the free carboxylic acid with amine can be carried out in the presence of one of the coupling agents, preferably as e.g. DCC or other dialkyl carbodiimides, carbonyldiimidazole, 1,2-oxazolinium compounds, e.g. 2-ethyl-5-phenyl-1,2-oxazolium-3'-suphonate and 2-tert.-butyl-5-methylisoxazolium perchlorate, or a suitable acylamino compound, e.g. 2-ethoxy-1-ethoxy-carbonyl-1,2-dihydroquinoline, or activated phosphoric acid derivatives, bis (2-oxo-3-oxazolidinyl)phosphinic acid chloride or 1-benzotriazolyloxy-tris(dimethylamino)phosphonium hexafluorophosphate etc.

In the preferred embodiment of this invention, after N-protection of the C(5)-amino group, in case the protective group in compound of formula VI was removed during the reduction/hydrogenation step(s), the lactone of formula VII can also be directly reacted with e.g. $NH_2CH_2C(CH_3)_2CONH_2$. as was shown in U.S. Pat. No. 5,559,111 or in EP-A-678 503 (p. 124, 130 and 131) or WO02/02508 (example H1 p. 35, preparation of J1) or U.S. Pat. No. 5,559,111 (example 83, page 22-25) or WO2006/024501 (page 46-47).

As a important embodiment of the invention, the hydroxamic ester function —C(=O)—$NOR^2$ in compounds of formulas II, III and IV represents simultaneously activation and protective group together: The novel bicyclic compounds of formula II and IV are the key elements in the invention because during deprotonation and alkylation of the compound of formula II with isopropylhalide, the hydroxamic ester function protects nitrogen and simultaneously facilitates the alkylation reactions. Furthermore, during the reaction of the compound of formula IV with compound of formula V this functional group increases reactivity of the hydroxamic ester function significantly against lactone, activation known as "Weinreb amide activation" (s. e.g. Tetrahedron Letters 1981, 22, 3815 or Org. Letters 2005, 7, 1427). Weinreb amides possess high reactivity very close to acid chlorides and are significantly more reactive than lactones: Therefore, organometalic reagent of formula V opens only the 5-membered ring containing hydroxamic ester, selectively.

As a further embodiment of the invention, instead of the above described reaction of the organometallic compound of formula V with compound of formula IV, polarity of both reaction components can also be reversed: According to this approach the activated 5-membered ring lactam of formula IV can be selectively opened and, after protection of the nitrogen function (—$NHOR^2$), the free carboxylic acid activated by converting into corresponding acid chloride or bromide or mixed anhydride, preferably chloride or —$OCOCF_3$ or —OMesyl or —$OSO2CF_3$, which then undergoes Friedel-Crafts reaction with a compound of formula V, wherein $R^1$ is —$COCF_3$, trifluoromethane sulphonyl-, Tosyl- or Mesyl- (Tetrahedon Letters 2002, 43, 7077) and $R^3$ is hydrogen, in the presence of Lewis acid, as commonly used for F—C.-reactions e.g. aluminium chloride, bortrifluoro etherate, metal halide, preferably $AlCl_3$, $ZnCl_2$, $BiCl_3$ or aluminium dodecatungsttophosphate (Tetrahedron Letters 2003, 44, 2937, ibid. 2003, 44, 5343, Tetrahedron 2004, 60, 10843).

With some Lewis acid catalyst as e.g. $AlCl_3$, $ZnCl_2$, $BiCl_3$ even the bicyclic compound of formula IV can be used directly for Friedel-Crafts reaction with compound of formula V. After F.-C. reaction the reaction sequence, as shown in Scheme 1, can be accomplished in the same way and in any stage of the synthesis the protective/deactivation $R^1$-group, trifluoromethane sulphonyl, Mesyl or Tosyl, can be removed and replaced by a group as defined for compound of formula I. As solvent for Friedel-Crafts-reaction commonly used aprotic inert organic solvents, preferably chlorinated hydrocarbons as methylenechloride or aliphatic hydrocarbons as hexane or heptane, can be used.

As a further embodiment of the invention, the starting compound of formula II can be prepared in many different ways, preferably as shown in Scheme 2:

Prochiral bislactone of formula VIII can be prepared from known cis- or trans dicarboxylic acid of formula XIV or XVIII, respectively or compounds of formulas XV, XVI and XVII or L-Ascorbic acid (J. Org. Chem. 1975, 40, 1936, ibid. 1990, 55, 5336, JACS 1959, 81, 3677, ibid. 1959, 81, 3677, ibid. 1959, 81, 3681, Tetrahedron Letters 1980, 21, 1819).

Desymmetrization of the prochiral bislactone of formula VIII (Tetrahedron Letters 1986, 27, 5437, ibid. 1999, 40, 1253, ibid. 1997, 38, 5249, Synlett 1995, 1029, Angew. Chem Int. 2006, 45, 7199, Org. Biomol. Chem. 2009, 7, 238, Eur. J. Org. Chem. 2004, 3884, J. Org. Chem. 2003, 68, 747) by a selective opening of one lactone ring followed by introduction of nitrogen containing functional group (any amine precursor) provides an excellent approach to chiral compound of formula II:

The desymmetrization can be achieved in many ways using either chiral reagent, as e.g. chiral amine and alcohol, or using a chiral solvent or using a chiral catalyst (e.g. J. Am. Chem. Soc. 1996, 118, 1809) including also enzymes as already reported sufficiently on various prochiral substrates (J. Org. Chem. 1996, 61, 1219).

Preferably, the prochiral bislactone of formula VIII can be opened stereoselectivly with water, alcohols, amines or hydroxylamine derivatives, preferably water, methanol, hydroxylamine or $NH_2OCH_3$, in the presence of chiral catalysts especially enzymes as lipase or protease. After desymmetrization chiral intermediates of formula IX,

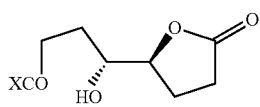

IX wherein X represents hydroxy, alkoxy, arylalkoxy, $NH_2$, lower alkyl amine, arylalkyl amine, —NHOH or —NHOalkyl, —NHOalkylaryl, preferably methoxy, —NHOMe, —NHObenzyl, are converted in one or more steps, after prior activation of C(3)-hydroxy group followed by simultaneous ring closure, into the bicyclic compound of formula II or formula X (WO2008/119804, p. 4) dependent on substitution X:

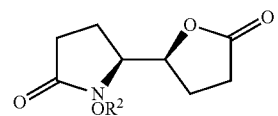

II

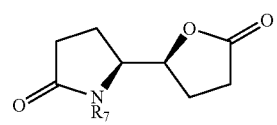

X

Activation of the C(3)-hydroxy group can be achieved with either Mitsunobu reaction ($PPh_3$ and dialkylazodicarboxylate) or via conversion of hydroxy group into corresponding mesylate, tosylate or triflate thereof: During spontaneous ring closure the configuration on the C(3)-carbon atom is inverted ($S_{N2}$-displacement) providing enantiomerically pure compound of formula II with the correct configuration.

As a further embodiment of the invention the compounds of formulas II or X can be prepared by rearrangement from known compound of formula XIII (U.S. Appl. No. 61/279, 995 Oct. 29, 2009) in the catalytic presence of transition metals or Lewis acids comprising initial base or acid catalyzed opening of 6-membered lactone and lactam rings followed by kinetic controlled ring closure.

In another reaction sequence comprising opening of lactam and lactone rings under basic condition with alkali metal hydroxides and subsequent double re-closure, preferably under acidic conditions, compound of formula XIII can also be converted into compounds of formula II or X.

In alternative approach nitrogen in the compound of formula XIII can be first protected with common N-protective group as e.g. BOC or Cbz-groups facilitating base catalyzed lactam opening followed by simultaneous intramolecular opening of the lactone ring and kinetically controlled ring closure, preferably under acidic conditions, leading to the thermodynamically more preferred compound of formula II or X.

As a further embodiment of the invention (Scheme 3), chiral compound of formula XII (described in WO 2007/045420 and used for synthesis of Aliskiren), wherein $R^7$ represents hydrogen, alkyl, aryl, alkylaryl, arylalkyl, trialkylsilyl, with heteroatom(s) substituted aryl, alkylaryl, preferably benzyl, mono-, di- or tri-methoxybenzyl or other N-protective group, in particular one which together with N forms an amid or carbamate, as —C(O)-alkyl, —C(O)-aryl, —C(O)-alkylaryl, —C(O)-arylalkyl, —C(O)—Oalkyl, —C(O)—Oaryl, —C(O)—Oalkylaryl, —C(O)—Oarylalkyl, preferably formyl, —C(O)Obenzyl (Cbz) or —C(O)O-tert.butyl (BOC) or trifluoracetate, can be prepared from a compound of formula X, wherein $R^7$ is the same as defined for compound of formula XII, by a) either deprotonation with a strong organic or inorganic base, preferably organic lithium or sodium amide as LDA or LiHMDS or NaHMDS, followed by alkylation with isopropylbromide or iodide b) or alternativly by condensation with acetone, followed by dehydration and reduction/hydrogenation similar as shown above for compound of formula IV.

Scheme 3

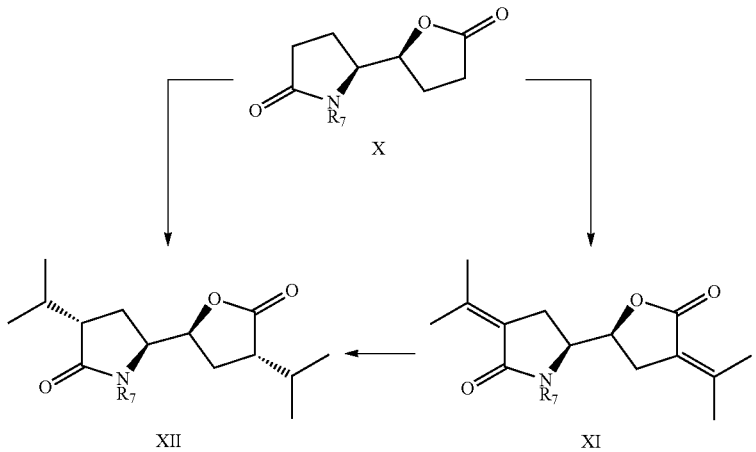

When referring to compounds described in the present invention, it is understood that references are also being made to salts thereof.

The example are provided to illustrate particular aspects of the disclosure and do not limit the scope of the present invention as defined by the claims.

EXAMPLES

Determination of optical purity was carried out with HPLC using chiral columns as Chiralcel OJ-H, Chiralpak AS-H or Chiralpak AD-H from Daicel Chem. Ind. In some cases the optical purity was also determined with NMR-Spectroscopy using chiral Eu-shift reagents.

Example 1

Preparation of Compound (IVa) from Compound (IIa)

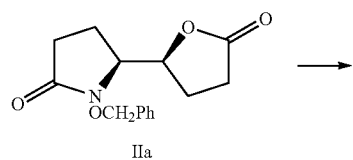

-continued

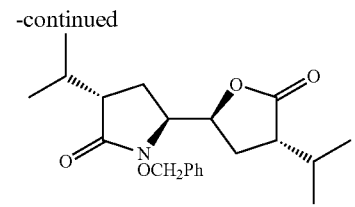

A 1.56 M solution of butyllithium in hexane (130 ml) was added over ca. 15 min under good stirring in an atmosphere of dry nitrogen to a cooled (−40° C.) solution of dry diisopropylamine (23 g) in dry THF (200 ml). To this solution, stirred for ca. 10 min at −40° C., a solution of compound (IIa) as shown above (27.6 g), dissolved in dry THF (75 ml), was added at the rate that reaction temperature did not exceed −40° C. Stirring was continued at −40° C. for ca. 30 min. To this slurry diisopropyl iodide (50 g) was added slowly and the temperature kept at under −40° C., the reaction mixture stirred for another 60 min, wormed up to ca. −10° C. and stirred for 2 hrs. The reaction mixture was poured on water (500 ml), the aqueous phase extracted 4times with ethylacetate (4×150 ml), the combined organic phases washed with brine, dried with sodium sulfate, filtered and evaporated under reduced pressure providing the title compound (IVa) as a single diastereomer: 31 g (86% yield) as a colorless oil. MS (M$^+$ 343), Anal. calculated for $C_{21}H_{29}NO_4$: C 70.17; H 8.13; N 3.90; O 17.80. Found: C 70.01; H 8.22; N 4.04; O 17.60.

Preparation of Compound (Ia, Aliskiren) from Compound (IVa)

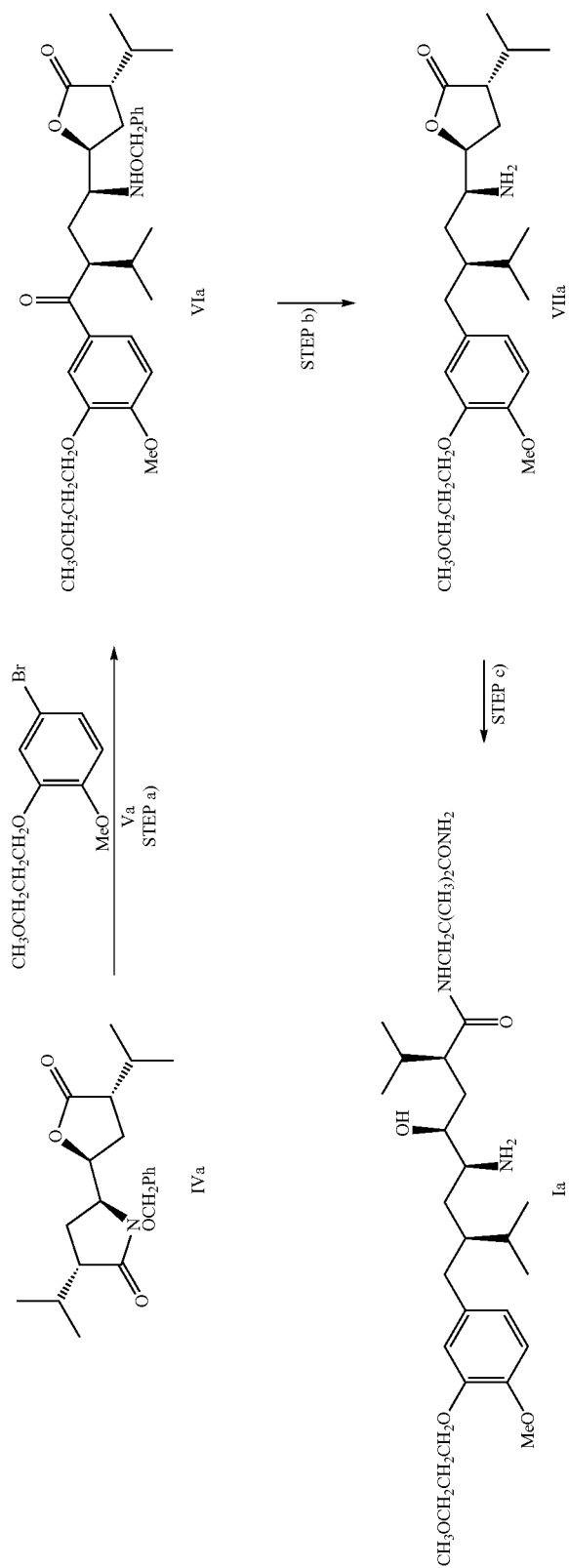

Example 2 a1) Preparation of Compound (VIa) from (IVa) Via Grignard Reagent:

Several crystals of iodine were added to a suspension of magnesium turnings (5.5 g) in THF (150 ml) and the mixture was stirred at rt under nitrogen for ca. 3 hrs, then 10 drops of 1,2-dibromo butane were added and the mixture stirred for another 30 min. To this slurry compound (Va) (28 g), dissolved in dry THF (50 ml), was slowly added under stirring that the reaction mixture started to reflux. When the addition was complete the reaction mixture was maintained under reflux for 1 hr. The reaction mixture was then cooled to rt and added dropwise within a period of ca. 1 hr to a solution of compound (IVa) (36 g) and dry $CeCl_3$ (3 g), dissolved in dry THF (150 ml) and cooled to $-78°$ C. The slurry was then further stirred at $-78°$ C. for 2 hrs, then wormed to $-35°$ C., stirred at this temperature 4 hrs, acetic acid (25 ml) was added at the same temperature and the mixture finally poured on saturated ammonium chloride solution (100 ml). After dilution with water (500 ml) the aqueous phase was extracted 4 times with ethyl acetate (4×100 ml), the combined organic phase washed once with saturated sodium bicarbonate solution (200 ml), dried over magnesium sulphate, filtrated and the solvents evaporated under reduced pressure providing the title compound (VIa) as a single diastereomer: crude 45 g (81% isolated yield) as a yellow oil. MS ($M^+$ 555): Small sample of the crude (VIa) was purified by a column chromatography on silicagel, eluens: hexane/ethyl acetate (5:1): Anal. calculated for $C_{32}H_{45}NO_7$: C 69.16; H 8.16; N 2.52; O 20.15. Found: C 69.10; H 8.11; N 2.6; O 20.45.

Example 3 a2) Preparation of Compound (VIa) from (IVa) Using Lithium Reagent:

To a solution of compound (Va) (30 g) dissolved in dry THF (250 ml), cooled to $-78°$ C., 1.56 M solution of butyl lithium (80 ml) was slowly added under stirring that the reaction temperature was kept at $-70°$ C., then the solution stirred at this temperature for 1 hr before dry $CeCl_3$ (2 g), dissolved in dry THF (10 ml), was added. This reaction mixture was then added dropwise within a period of ca. 1 hr to a stirred solution of compound (IVa) (35 g), dissolved in THF (200 ml) and cooled to $-40°$ C. After stirring for 2 hrs at $-40°$ C. the mixture was poured on saturated sodium bicarbonate solution (300 ml), the aqueous phase extracted 4 times with ethyl acetate (4×150 ml), the combined organic phases washed once with saturated sodium bicarbonate solution (400 ml), dried over magnesium sulphate, filtrated and the solvents evaporated under reduced pressure providing the title compound (VIa) as a single diastereomer: crude 44 g as a yellow oil having the same data as shown above in Example 2, part a1).

Example 4 b) Preparation of Compound (VIIa) from (VIa):

Compound (VIa) (5.5 g) was dissolved in glacial acetic acid (50 ml) and two drops of concentrated HCl and 10% Pd—C (800 mg) were added. The slurry was under intensive stirring hydrogenated under normal pressure at rt for ca. 3 hrs until more than 3 equivalents of hydrogen have been consumed. After filtration of the catalyst, the filtrate was acidified with conc. HCl to pH ca. 1 and the solvent evaporated under reduced pressure providing crude compound (VIIa) as hydrochloride as a brawn oil: 5.6 g. This crude material was directly used for the next step (Example 5).

Instead of 10% Pd—C in acetic acid also other hydrogenation catalysts can be used as $PtO_2$ or Ra—Ni in ethanol or THF or ethyl acetate.

Example 5 c1) Preparation of Compound (Ia, Aliskiren) from Compound (VIIa) Using Cbz-Protective Group:

Crude compound (VIIa) as hydrochloride from the above experiment (Example 4) (5.6 g) was dissolved in a mixture of aqueous saturated sodium bicarbonate solution and THF (60 ml, 1:3) and to this stirred solution chloroformate benzyl ester (ca. 4 ml) was slowly added at rt to achieve complete Cbz-protection of the C(5)-amino function (ca. 2 hrs). The Cbz-protected lactone VII was then isolated by pouring the reaction mixture on water (300 ml) and extraction 3 times with ethyl acetate (3×50 ml), drying the organic phase with magnesium sulphate, filtration of the organic solution and evaporation under reduced pressure: The crude Cbz-protected lactone [(1S,3S)-1-((2S,4S)-4-isopropyl-5-oxo-tetrahydrofuran-2-yl)-3-[4-methoxy-3-(3-methoxypropoxy)-benzyl]-4-methyl-pentyl]-carbamic acid benzyl ester: (5.4 g) was directly converted into final compound (I).

A solution of the above prepared Cbz-protected lactone (5.4 g), 3-amino-2,2-dimethyl propionamide (1.5 g) and 2-hydroxypyridine (1 g) in tert.-butyl methyl ether (10 ml), containing triethylamine (0.2 ml), was stirred for 18 hrs at 80° C., then cooled to rt and diluted with toluene (20 ml) and washed with 10% sodium hydrogen sulphate solution (100 ml). The organic phase was separated, washed once with water (50 ml), dried with magnesium suphate, filtrated and evaporated under reduced pressure to give a yellow oil which was suspended in hexane (100 ml), slurry stirred a few min, filtrated and the filtrate evaporated under reduced pressure providing a foam of Cbz-protected derivative of Aliskiren (Ia): 4.5 g.

The crude Cbz-protected Aliskiren (4.5 g) was the dissolved in a mixture of glacial acetic acid and ethanol (40 ml, 1:1) and after addition of 10% Pd—C under intensive stirring the slurry was hydrogenated under normal pressure at rt. The reaction mixture was then filtered to remove the catalyst, poured on water (100 ml) and pH adjusted with 37% sodium hydroxide solution to 10. The final product, Aliskiren was then extracted 4times with dichloromethane (4×100 ml), the organic phase evaporated under reduced pressure providing crude Aliskiren (Ia): 4.0 g with identical analytical data as reported e.g. in EP 0678503 p. 74, example 137: MS($M^+$ 552), Rf 0.33 on silicagel eluens: dichloromethane/methanol=8:2.

From the free base (Ia) the hemifumarate salt can be prepared, e.g. as described in U.S. Pat. No. 6,730,798 example J1.

Example 6 c2) Preparation of Compound (Ia, Aliskiren) from Compound (VIIa) Using BOC Protective Group:

Crude lactone (VIIa) hydrochloride from the above experiment (Example 4) (5.6 g) was dissolved in THF (40 ml), N,N-dimethyl aminopyride (0.1 g) triethylamine (4 g) and di-tert-butyldicarbonate (3 g) were added at rt and the mixture stirred for 24 hrs to achieve complete BOC-protection of the C(5)-amino group. After careful acidification of the reaction mixture with glacial acetic acid, the mixture was extracted with toluene/water mixture and the organic phase separated and evaporated under reduced pressure: 4.1 g of BOC-protected lactone [(1S,3S)-1-((2S,4S)-4-isopropyl-5-oxo-tetrahydro-furan-2-yl)-3-[4-methoxy-3-(3-methoxypropoxy)-benzyl]-4-methyl-pentyl]-carbamic acid tert.-butyl ester. The analytical data were identical as reported e.g. in WO2006/024501, p. 58).

A solution of the BOC-protected lactone VII (4.1 g), 3-amino-2,2-dimethyl propionamide (1.5 g) and 2-hydroxy-pyridine (1 g) in tert.-butyl methyl ether (20 ml), containing triethylamine (0.2 ml), was stirred for 18 hrs at 80° C., then cooled to rt and diluted with toluene (20 ml) and washed with 10% sodium hydrogen sulphate solution (100 ml). The organic phase was separated, washed once with water (50 ml), dried with magnesium suphate, filtrated and evaporated under reduced pressure to give a yellow oil which was suspended in hexane (100 ml), slurry stirred a few min, filtrated and the filtrate evaporated under reduced pressure providing a foam of BOC-protected derivative of Aliskiren (Ia): 4.5 g.

The crude BOC-protected Aliskiren (4.5 g) was dissolved in a solution of trifluoroacetic acid and dichloromethane (30 ml, 1:5) at rt, stirred for 2 hrs and then pH adjusted to 10 with 37% sodium hydroxide solution. The aqueous phase was extracted 3times with dichloromethane (3×100 ml), dried with magnesium sulphate, filtrated and the filtrate evaporated under reduced pressure providing yellow oil of Aliskiren (Ia): 3.1 g: The analytical date were identical with reported in EP 0678 503, example 137.

The invention claimed is:
1. A process for the preparation of a compound of general formula I

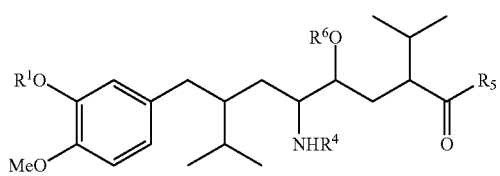

wherein
$R^1$ represents hydrogen, linear or branched $C_{1-6}$ alkyl, $C_{1-6}$ alkoxy-$C_{1-6}$ alkyl, alkylaryl, arylalkyl, or acyl or carbamoyl, trifluoracetyl, mesyl, tosyl, trifluoromethanesulfonyl, trialkylsilyl or alkylarylsilyl;
$R^4$ represents hydrogen, arylalkyl, alkoxy, arylalkoxy, trialkylsilyl, alkylarylsilyl, with heteroatom(s) substituted arylalkyl, or other N-protective group;
$R^5$ represents hydroxy, linear or branched $C_{1-6}$ alkyloxy, aryloxy, alkylaryloxy, arylalkyloxy, trialkylsilyloxy or alkylarylsilyloxy, halogen,
—$NH_2$, —$NMe_2$, —$NHCH_2C(CH_3)_2CONH_2$
$R^6$ represents hydrogen, arylalkyl, trialkylsilyl, alkylarylsilyl, with heteroatom(s) substituted alkyl, arylalkyl, or other O-protective group;
comprising following steps:
a) reaction of the compound of formula II, wherein $R^2$ represents hydrogen, alkyl, aryl, alkylaryl, arylalkyl, trialkylsilyl, alkylarylsilyl, with heteroatom(s) substituted alkyl, aryl, alkylaryl, arylalkyl, or other O-protective group,

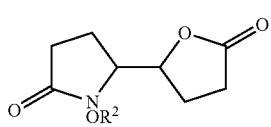

either
aa) with acetone under basic conditions followed by dehydration step providing the compound of formula III

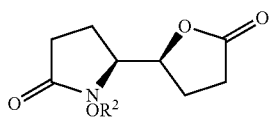

followed then by reduction or hydrogenation of the double bond or
or
bb) with a strong organic or inorganic base, preferably organic lithium or sodium amide as e.g. LDA, or LiHMDS or NaHMDS, followed by alkylation with isopropyl halide, preferably bromide or iodide,
providing compound of formula IV

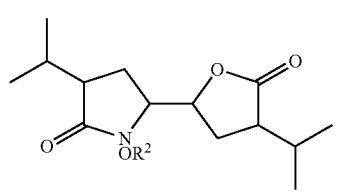

b) reaction of the compound of formula IV with a compound of formula V,

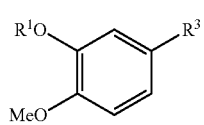

wherein $R^1$ is the same as defined for compound of formula I and $R^3$ is a metal containing group such as —Li, —Na, —Mghalide, Znhalide, —Cehalides, boronic acid as —$B(OH)_2$, cuprate or —Cuhalide, providing a compound of formula VI

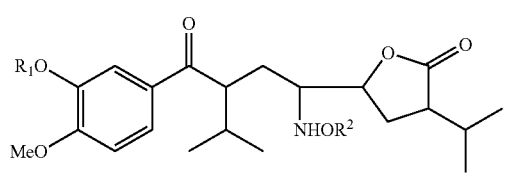

c) hydrogenation or/and reduction of C(8)-oxo and C(5)-hydroxylamine group in the compound of formula VI, either simultaneously or in separate steps, to a compound of formula VII,

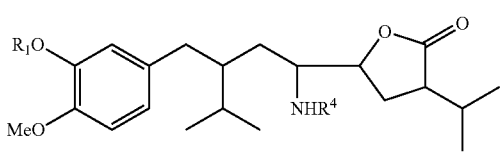

wherein $R^1$ is the same as defined for compound of formula I and $R^4$ is hydrogen, trialkylsilyl, alkylarylsilyl;
d) protection of the C(5)-amino group, followed by either
aa) hydrolysis of the lactone of formula VII and subsequent reaction of the free carboxylic acid with a peptide coupling reagent and then reaction with $R^5$—H, wherein $R^5$ is the same as defined for the compound of formula I, or
bb) by direct reaction of the lactone of formula VII with $R^5$—H.

2. A process according to claim 1, wherein the compound of formula I has the configuration as given

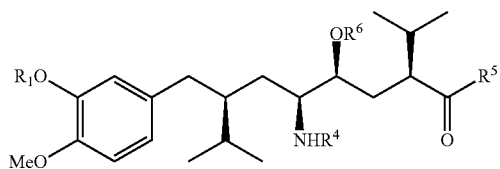

and the compounds of formulas II, III, IV, VI and VII have the configuration as

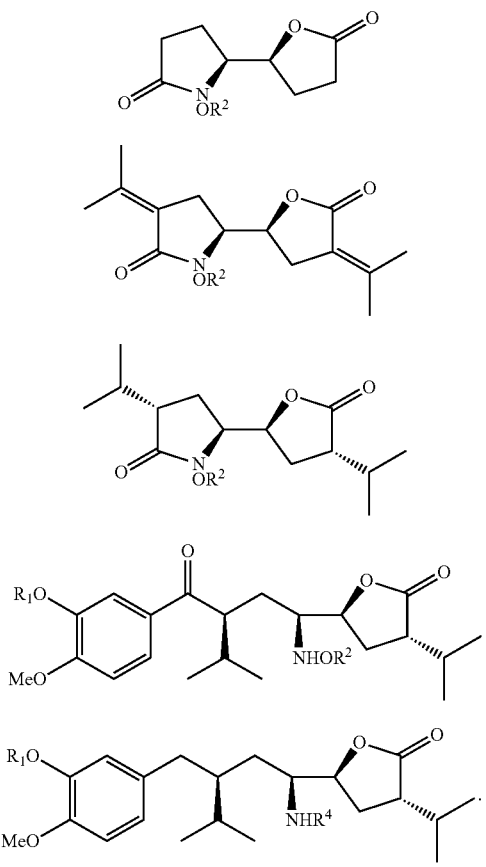

3. A process according to claim 1 or 2, wherein $R^2$ is hydrogen, lower alkyl, alkylaryl, preferably hydrogen, methyl, ethyl, benzyl, dimethoxybenzyl or trialkylsilyl.

4. A process according to claim 1, wherein in compounds of formulas I, II, Ill, IV, V, VI and VII
   $R^1$ represents $CH_3OCH_2CH_2CH_2$—,
   $R^2$ represents hydrogen, lower alkyl or alkylaryl, benzyl, 2,4-dimethoxybenzyl, acetyl, Cbz- or BOC-protective group,
   $R^3$ represents Lithium, magnesium-chloride or bromide,
   $R^4$ and $R^6$ represent hydrogen, acetyl, formyl, —C(O)OMe, —C(O)Obenzyl (Cbz), —C(O)Otert.butyl (BOC), trifluoracetyl,
   $R^5$ represents hydroxy, lower alkyloxy, benzyloxy or —$NHCH_2C(CH_3)_2CONH_2$.

5. A process according to claim 2, wherein the compound of formula IV

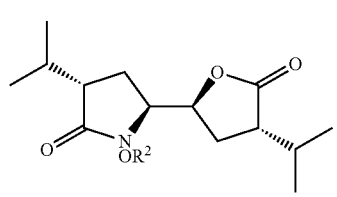

is prepared by reacting the compound of formula II

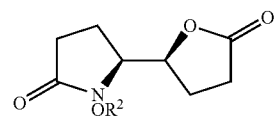

with either
aa) acetone under basic conditions followed by dehydration step providing a compound of formula III

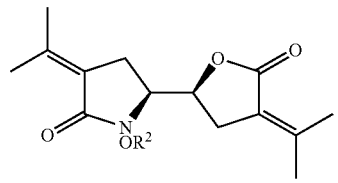

followed by reduction or hydrogenation of the double bond, or
bb) a strong organic or inorganic base, followed by alkylation with isopropyl halide, preferably bromide or iodide.

* * * * *